(12) United States Patent
Baurys et al.

(10) Patent No.: US 12,702,557 B2
(45) Date of Patent: Aug. 11, 2026

(54) ANCHORING NAILS AND SYSTEMS

(71) Applicant: NuVasive, Inc., San Diego, CA (US)

(72) Inventors: Joseph W. Baurys, Raleigh, NC (US); Elizabeth L. Ovrom, San Diego, CA (US); Steven Lillig, San Diego, CA (US)

(73) Assignee: Nuvasive, Inc., San Diego, CA (US)

( * ) Notice: Subject to any disclaimer, the term of this patent is extended or adjusted under 35 U.S.C. 154(b) by 134 days.

(21) Appl. No.: 18/592,702

(22) Filed: Mar. 1, 2024

(65) Prior Publication Data

US 2024/0299176 A1 Sep. 12, 2024

Related U.S. Application Data

(60) Provisional application No. 63/450,711, filed on Mar. 8, 2023.

(51) Int. Cl.

| | |
|---|---|
| ***A61F 2/30*** | (2006.01) |
| ***A61B 17/84*** | (2006.01) |
| ***A61B 17/92*** | (2006.01) |
| ***A61F 2/44*** | (2006.01) |
| ***A61F 2/46*** | (2006.01) |

(52) U.S. Cl.

CPC ........ *A61F 2/30749* (2013.01); *A61B 17/846* (2013.01); *A61B 17/92* (2013.01); *A61F 2/4455* (2013.01); *A61F 2/4611* (2013.01); *A61F 2002/30131* (2013.01); *A61F 2002/30494* (2013.01); *A61F 2002/30825* (2013.01); *A61F 2002/30845* (2013.01); *A61F 2002/30985* (2013.01); *A61F 2002/4619* (2013.01)

(58) Field of Classification Search

CPC . A61B 17/8615; A61B 17/846; A61B 17/848; A61F 2/30749; A61F 2/4455; A61F 2220/0016

USPC .......................................... 600/210; 606/239

See application file for complete search history.

(56) References Cited

U.S. PATENT DOCUMENTS

| | | | | |
|---|---|---|---|---|
| 4,055,172 A * | 10/1977 | Ender | A61B 17/7208 | 606/62 |
| 4,135,506 A * | 1/1979 | Ulrich | A61B 17/8872 | 606/86 R |
| 4,373,518 A * | 2/1983 | Kaiser | A61B 17/1615 | 606/329 |

(Continued)

FOREIGN PATENT DOCUMENTS

| | | |
|---|---|---|
| JP | 2016524988 A | 8/2016 |
| JP | 2017529910 A | 10/2017 |

(Continued)

*Primary Examiner* — Eduardo C Robert

(57) ABSTRACT

Various implementations include anchoring nails, fixation apparatuses, spinal fixation systems, and related methods described in this disclosure. Certain implementations include a fixation nail for an interbody fusion procedure, the fixation nail including: a body having an arcuate primary axis extending from a distal end to a proximal end thereof, the body having an outer surface that enables complete insertion and removal of the fixation nail into an interbody without threaded engagement, and the body further including an elongated recess spanning a majority of a length of the body, the elongated recess sized to at least partially encompass at least one of tissue or bone during insertion into a patient.

19 Claims, 15 Drawing Sheets

(56) References Cited

U.S. PATENT DOCUMENTS 5,672,178 A * 9/1997 Petersen ................ A61B 17/68 606/907
6,723,128 B2 * 4/2004 Uk .......................... A61F 2/446 623/17.15
7,837,694 B2 * 11/2010 Tethrake ................ A61B 90/98 606/79
8,287,577 B2 * 10/2012 Berberich .......... A61B 17/0401 606/329
8,641,766 B2 * 2/2014 Donner ................... A61F 2/442 606/279
9,044,337 B2 * 6/2015 Dinville ................ A61F 2/4455
9,351,847 B2 * 5/2016 Reed ..................... A61F 2/4611
9,517,144 B2 * 12/2016 McAtamney ....... A61F 2/30749
9,987,142 B2 * 6/2018 McConnell ........... A61F 2/4455
10,137,005 B2 * 11/2018 Ashleigh ............... A61F 2/4611
10,238,504 B2 * 3/2019 Mesiwala ............. A61F 2/4611
10,758,370 B2 * 9/2020 Gilbride ............. A61B 17/8685
10,898,345 B2 * 1/2021 Bergey .................. A61F 2/4455
11,154,406 B2 * 10/2021 Joly .................... A61F 2/30771
11,576,785 B1 2/2023 Cummins
11,883,076 B2 * 1/2024 Glerum ................. A61F 2/4455
2006/0232408 A1 * 10/2006 Nycz ...................... A61B 90/90 340/572.1
2010/0185289 A1 * 7/2010 Kirwan ................... A61F 2/447 623/17.11
2011/0098747 A1 * 4/2011 Donner .............. A61B 17/7044 606/264
2011/0208311 A1 * 8/2011 Janowski .............. A61F 2/4425 623/17.16
2014/0031881 A1 * 1/2014 Bales ................... A61B 17/846 606/329
2014/0114415 A1 * 4/2014 Tyber .................... A61F 2/4455 623/17.16
2015/0209089 A1 7/2015 Chataigner et al.
2016/0058563 A1 3/2016 Zappacosta et al.
2016/0148027 A1 * 5/2016 Schoutens ........ G06K 19/07749 340/10.1
2016/0250037 A1 9/2016 Duffield et al.
2018/0042732 A1 * 2/2018 Seifert .................. A61F 2/4611
2018/0303623 A1 * 10/2018 Shoshtaev ............... A61F 2/447
2020/0093565 A1 * 3/2020 Birchler ................. A61B 90/94
2020/0138595 A1 * 5/2020 Shoshtaev ............... A61F 2/447
2020/0297511 A1 * 9/2020 Gray ...................... A61B 17/86
2020/0405362 A1 * 12/2020 Faulhaber .......... A61B 17/7032
2021/0059834 A1 3/2021 Miguel et al.
2021/0085483 A1 * 3/2021 MacMillan ......... A61F 2/30749
2021/0267766 A1 9/2021 McConnell
2022/0087820 A1 3/2022 Lee et al.
2022/0370203 A1 11/2022 McIver et al.
2025/0339277 A1 * 11/2025 Bohenick ........... A61B 17/8615
2026/0060806 A1 * 3/2026 Villasana ............ A61F 2/30749

FOREIGN PATENT DOCUMENTS

JP 2022540593 A 9/2022
WO 2015009793 A1 1/2015
WO WO-2019022976 A1 * 1/2019 ............ A61F 2/4611
WO 2022061302 A1 3/2022

* cited by examiner 230
250
300
10
260A
280
270
250
262
260B
240
242
$a_{pi}$ $a_{pn}$
160
10
250

270
270
$a_{pn}$
240
260A
262
240
250
262
260B
230
240
$a_{pi}$

ANCHORING NAILS AND SYSTEMS

CROSS-REFERENCE TO RELATED APPLICATION(S)

This present application is a non-provisional application and claims priority to provisional application No. 63/450,711, filed on Mar. 8, 2023, which is incorporated by reference herein in its entirety for all purposes.

TECHNICAL FIELD

This disclosure generally relates to medical devices. More particularly, the disclosure relates to the field of spinal surgery and spinal fixation devices.

BACKGROUND

The spine is critical in human physiology for mobility, support, and balance. Spinal injuries can be debilitating or catastrophic to patients. Even small irregularities in the spine can cause devastating pain and loss of coordination.

Surgical procedures are commonly performed to correct problems with displaced, damaged, or degenerated intervertebral discs. Generally, spinal fusion procedures involve removing some or all of the diseased or damaged disc, and inserting one or more intervertebral implants into the resulting disc space. Successful replacement of injured or deteriorated spinal bone with artificial implants can involve consideration and understanding of the inherent stresses on the spine, as well as the biological properties of the body in response to the devices.

SUMMARY

The needs above, as well as others, are addressed by embodiments of anchoring (or, fixation) nails (also called anchoring or fixation "blades"), fixation apparatuses, spinal fixation systems, and related methods described in this disclosure. All examples and features mentioned below can be combined in any technically possible way.

Certain implementations include a fixation nail for an interbody fusion procedure, the nail having: a body having an arcuate primary axis extending from a distal end to a proximal end thereof, wherein the body has an outer surface that enables complete insertion and removal of the fixation nail into an interbody without threaded engagement, and the body includes an elongated recess spanning a majority of a length of the body, the elongated recess sized to at least partially encompass at least one of tissue or bone during insertion into a patient.

In particular aspects, a system includes: an interbody for placement in a patient's spinal column, the interbody including at least one through-hole; a nail sized for placement within the at least one through-hole; and a nail guide configured to deploy the nail to the at least one through-hole in the interbody, wherein the nail guide includes at least one biasing mechanism for deploying the nail without a threaded connection to the interbody.

In additional particular aspects, a method of placing an interbody in a patient's spinal column includes: inserting the interbody between discs in the patient's spinal column; pre-loading a nail guide with a nail positioned to engage the interbody and the patient's spinal column; and deploying the nail from the nail guide to fix the interbody to the patient's spinal column, wherein the nail has a body with an elongated recess spanning a majority of a length of the body, the elongated recess sized to at least partially encompass at least one of tissue or bone during deployment of the nail into the patient's spinal column.

Implementations may include one of the following features, or any combination thereof.

In certain examples, the outer surface of the body is thread-free. In some cases, the thread-free outer surface of the body enables thread-free engagement of the interbody and the vertebral body and/or bone of the patient.

In particular aspects, the elongated recess extends along the arcuate primary axis of the body. In certain aspects, the elongated recess envelopes, captures and/or contains a portion of the tissue and/or bone of the patient during deployment of the nail into the patient's spinal column. In certain examples, the recess can act to contain a portion of the tissue and/or bone. In further examples, the recess is sized to prevent plastic displacement of the bone, e.g., to capture a pocket of the bone.

In some cases, the body has a reduced thickness along the elongated recess.

In certain implementations, the elongated recess spans between separate wall sections of the body.

In some aspects, the separate wall sections have a combined width as measured across the arcuate primary axis, the elongated recess has a width as measured across the arcuate primary axis, and a ratio of the combined width of the separate wall sections to the width of the elongated recess is approximately 0.5:1 to approximately 2:1.

In particular implementations, the body includes a tri-point head near the proximal end for promoting insertion of the fixation nail into the patient.

In certain cases, at least one point in the tri-point head is proximal relative to another other point in the tri-point head.

In some aspects, two points in the tri-point head are approximately aligned in the distal-proximal direction.

In particular aspects, the tri-point head provides a cutting surface during insertion of the fixation nail into the patient.

In certain implementations, the fixation nail is configured to be pre-loaded into a nail guide before insertion into the patient.

In certain cases, the body includes a fin extending at least partially axially along the arcuate primary axis to stabilize the fixation nail in the interbody.

In some implementations, the proximal end of the body includes a slot sized to receive a removal tool for removing the fixation nail from a nail guide.

In particular aspects, the body includes at least one approximately flat section proximate the slot for engaging a biasing mechanism on the interbody.

In some cases, the slot has a keyed shape.

In certain aspects, the keyed shape enables selective loading or unloading of the fixation nail from the nail guide.

In particular implementations, the body is additively manufactured.

In some aspects, the fixation nail is one of a plurality of fixation nails of distinct size, and the body includes at least one indicator of a size of the fixation nail.

In certain cases, the fixation nail is compatible with a supine anterior lateral interbody fusion (ALIF) procedure and a lateral ALIF procedure.

In particular aspects, the at least one biasing mechanism includes a first biasing mechanism that controls deploying the nail to the at least one through-hole.

In some cases, the at least one biasing mechanism further includes a second biasing mechanism that prevents unintentional discharge of the nail from nail guide.

In certain implementations, the at least one biasing mechanism provides at least one of audible feedback or tactile feedback that the nail is secured in the nail guide.

In some aspects, a system further includes: an inserter for engaging the nail guide; and an impactor coupled with the inserter for deploying the nail into the interbody.

In particular cases, the nail guide further includes a locking mechanism for engaging a complementary locking mechanism on the inserter.

In certain aspects, the locking mechanism includes a multi-segment slot and the complementary locking mechanism includes a tab complementing a portion of the multi-segment slot.

In particular implementations, during deployment, the impactor drives the nail through the slot in the nail guide.

In some cases, the impactor has a primary axis that is off-axis relative to a primary axis of the nail.

In certain cases, the nail guide includes a depth stop for controlling a position of the interbody during deployment of the nail. In some examples, the depth stop is removable and/or reversible for flush or countersunk configurations.

In some cases, a system further includes a removal tool for engaging a proximal end of the nail via a non-threaded mechanism.

In certain aspects, the removal tool includes a protrusion sized to engage with a keyed slot in the proximal end of the nail in a first orientation and disengage with the keyed slot in the proximal end of the nail in a second orientation.

In particular implementations, the interbody includes a retention feature, and the removal tool further includes a ridge for engaging the retention feature to enable removing of the nail from the interbody.

In some cases, the nail is configured to be pre-loaded into the nail guide prior to insertion into the patient.

In certain implementations, the body includes a fin extending at least partially axially along the arcuate primary axis to stabilize the nail in the interbody.

In some cases, the system is used in a method of fixing the interbody in the patient's spinal column.

In certain implementations, pre-loading the nail guide with the nail includes inserting the nail in a through-hole in a nail guide, the nail guide having at least one non-threaded biasing mechanism for retaining the nail. In certain cases, inserting the nail in the through-hole is performed by hand.

In some cases, deploying the nail through the at least one through-hole in the nail guide is performed with an impactor, wherein the impactor has a primary axis that is off-axis with a primary axis of the nail during insertion.

Two or more features described in this disclosure, including those described in this summary section, may be combined to form implementations not specifically described herein.

The above presents a simplified summary in order to provide a basic understanding of some aspects of the claimed subject matter. This summary is not an extensive overview. It is not intended to identify key or critical elements or to delineate the scope of the claimed subject matter. Its sole purpose is to present some concepts in a simplified form as a prelude to the more detailed description that is presented later.

The details of one or more implementations are set forth in the accompanying drawings and the description below. Other features, objects and benefits will be apparent from the description and drawings, and from the claims.

Figure 1:
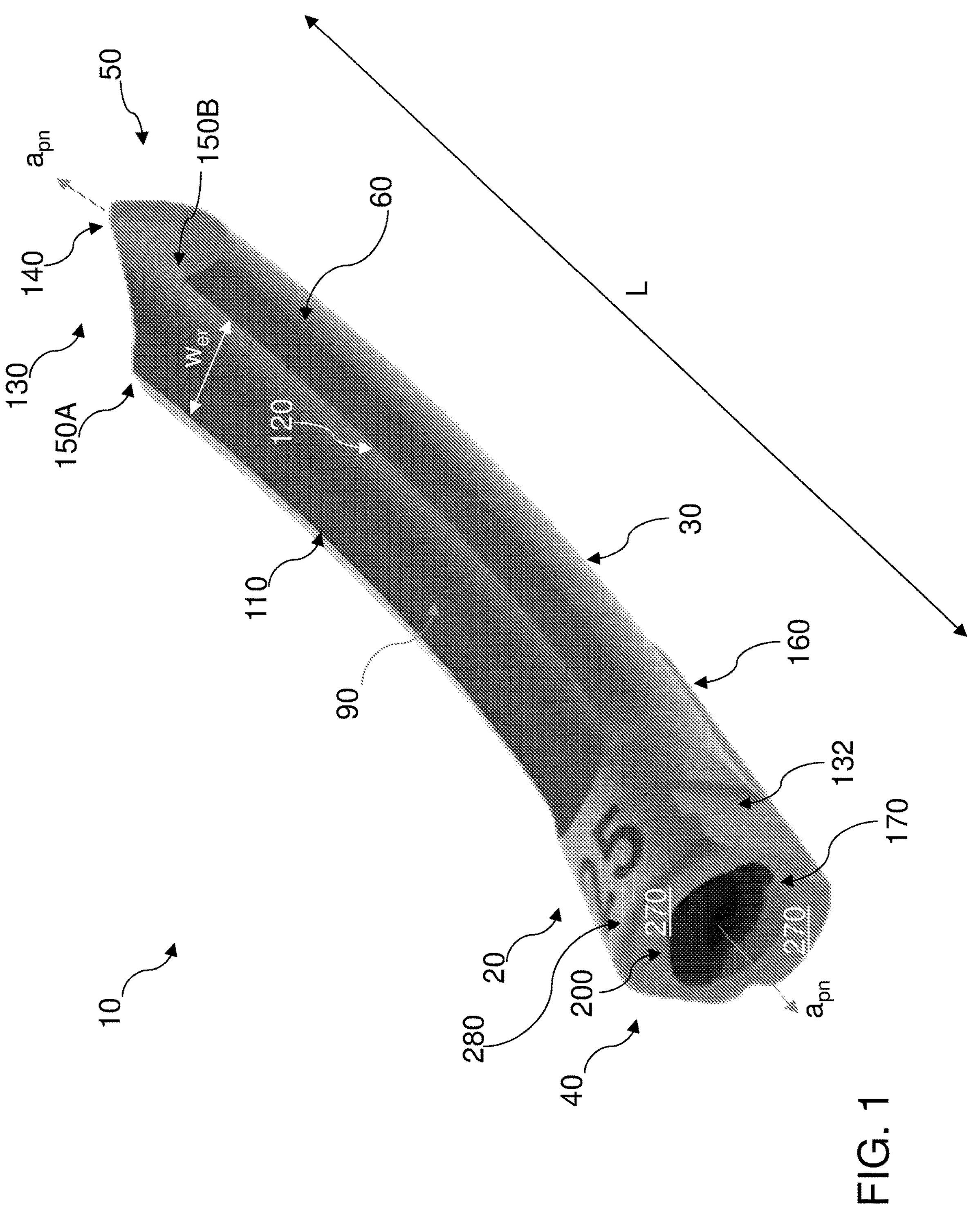
FIG. 1 shows a perspective view of a fixation nail according to various implementations.

It is noted that the drawings of the various implementations are not necessarily to scale. The drawings are intended to depict only typical aspects of the disclosure, and therefore should not be considered as limiting the scope of the implementations. In the drawings, like numbering represents like elements between the drawings.

DETAILED DESCRIPTION

Various example embodiments of devices and techniques for interbody fusion procedures are described herein. In the interest of clarity, not all features of an actual implementation are necessarily described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The devices, related systems, and methods described herein boast a variety of inventive features and components that warrant patent protection, both individually and in combination.

It is to be understood that any given elements of the disclosed embodiments of the invention may be embodied in a single structure, a single step, a single substance, or the like. Similarly, a given element of the disclosed embodiment may be embodied in multiple structures, steps, substances, or the like.

This disclosure provides, at least in part, a fixation nail for an interbody fusion procedure, related fixation (or anchoring) systems, methods and apparatuses that beneficially incorporate a nail with an elongated recess to at least partially encompass tissue and/or bone during insertion into a patient. This disclosure further provides a nail guide that is configured to deploy the nail to at least one through-hole in an interbody and includes at least one biasing mechanism to deploy the nail without a threaded connection to the interbody. The nail guide can be pre-loaded with the nail(s). The various disclosed implementations can improve patient outcomes when compared with conventional fusion procedures. For example, the disclosed aspects can improve operating room efficiency relative to conventional fusion procedures by reducing process steps. Disclosed aspects can also reduce incision size for a fusion procedure relative to conventional devices and systems. Further, disclosed aspects can improve procedural safety when compared to conventional fusion procedures by consolidating instrument functionality.

Commonly labeled components in the drawings are considered to be substantially equivalent components for the purposes of illustration, and redundant discussion of those components is omitted for clarity.

FIG. 1 is a perspective view of a fixation nail 10 (also called a "blade", or simply a "nail") for use in an interbody fusion procedure. Fixation nail 10 may include a body 30 having an arcuate primary axis ($a_p$) extending from a proximal end 40 to a distal end 50 of the body 30. In some non-limiting examples, the body 30 is additively manufactured. In various implementations, the body 30 has an outer surface 60 that enables complete insertion and removal of the nail 10 into an interbody 70 (FIGS. 3 and 4) without threaded engagement. That is, the outer surface 60 is thread-free in various implementations.

Figure 2:
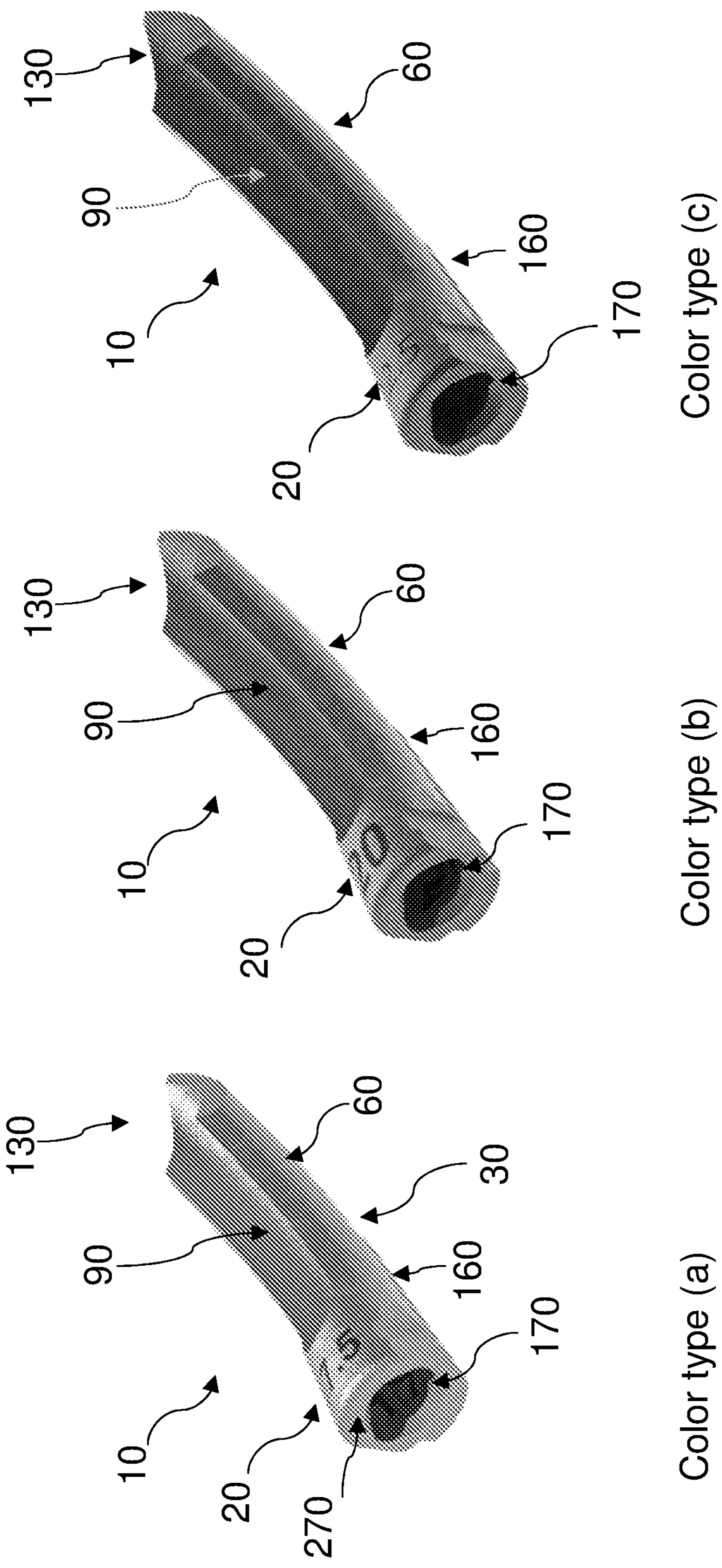
FIG. 2 shows distinct sized fixation nails according to various implementations.

FIG. 1 illustrates the fixation nail 10 in a first size, and FIG. 2 illustrates the fixation nail 10 in various additional sizes, each of which is an example of any practical number of sizes available for particular fusion procedures. In some embodiments, an indicator 20 can provide information on the distinct size of a respective fixation nail 10, e.g., a visual indicator such as a displayed size and/or a tactile indicator of the size. In certain cases, a color or pattern of the fixation nail 10 is an indicator of the size, e.g., as illustrated in the various colors (types (a), (b), (c)) shown in nails 10 in FIG. 2 as compared with one another and with the nail 10 in FIG. 1.

Figure 3:
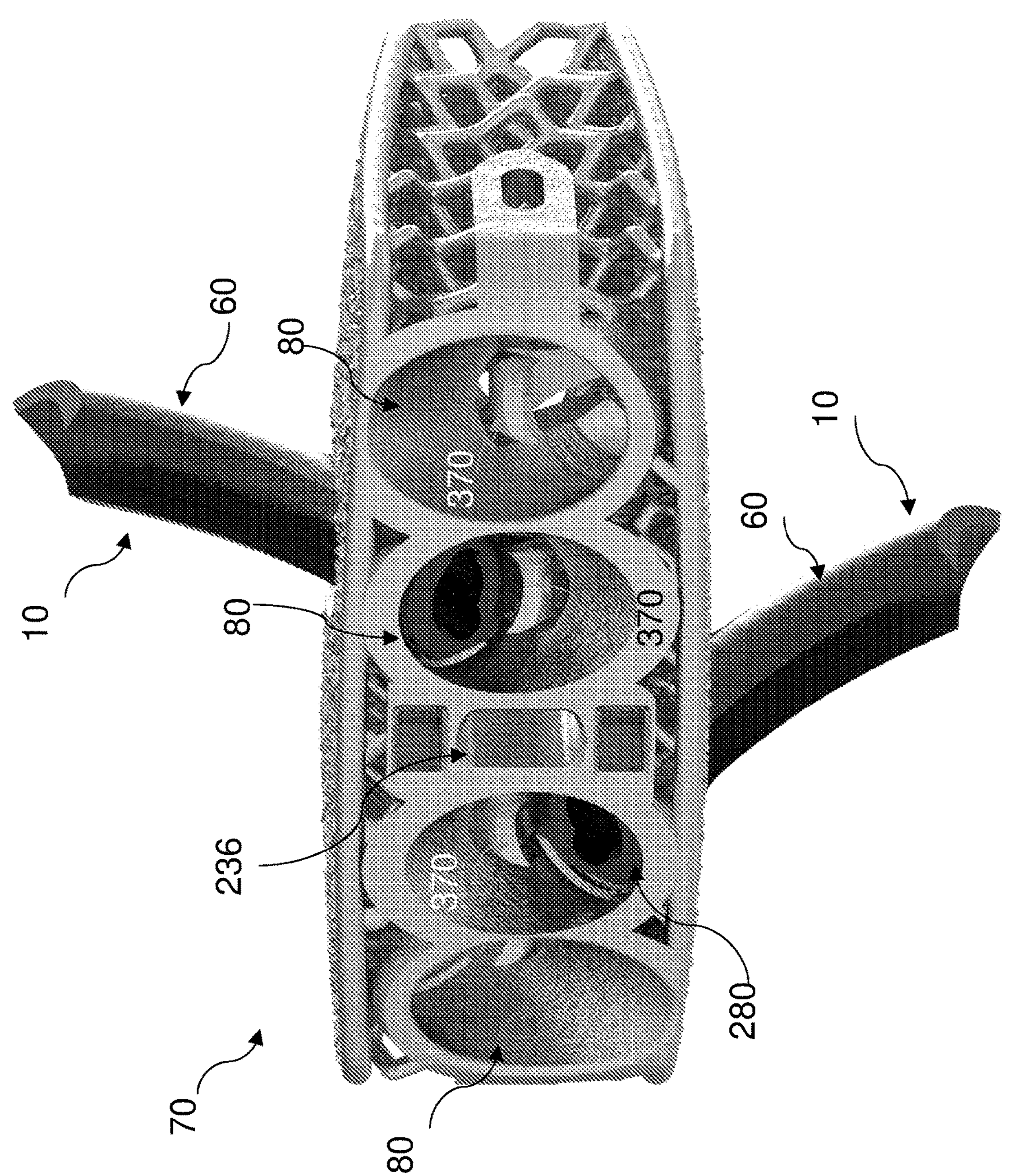
FIG. 3 shows a first perspective view of an interbody coupled with fixation nails according to various implementations.
Figure 4:
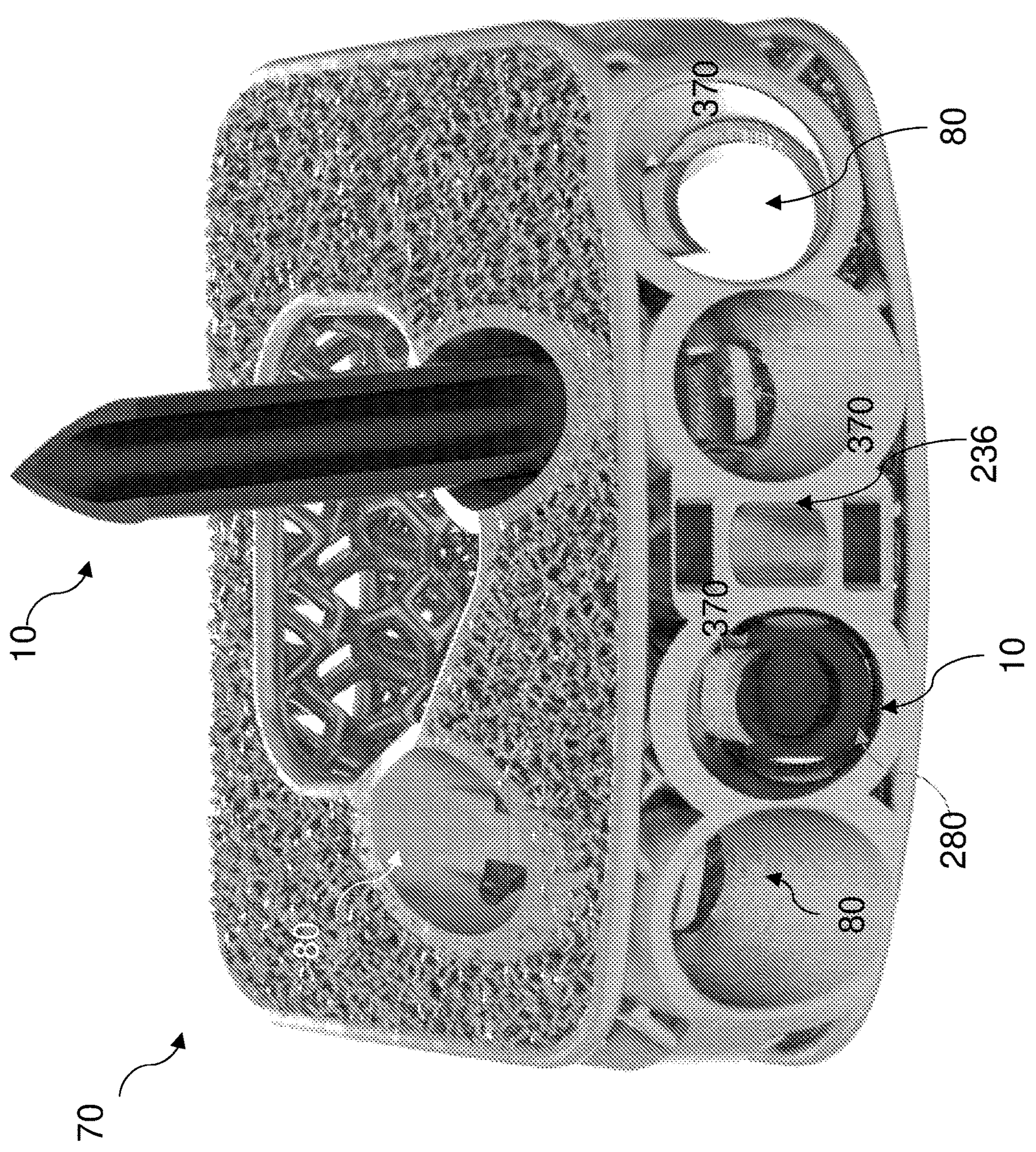
FIG. 4 shows a second perspective view of the interbody and fixation nails from FIG. 3.

FIGS. 3 and 4 illustrate side and perspective views, respectively, of an interbody 70 including a set of through-holes 80 for receiving and retaining the fixation nail 10. As described herein, the nail 10 can be completely inserted (and retained) in the interbody 70 without threaded engagement. It is understood that in an interbody fusion procedure, the nail 10 may also be inserted into the patient, e.g., to engage with the vertebral body. Additional details of an interbody fusion procedure are described, for example, in PCT Application No. US 2022/023224 (Spinal Implant with Flexible Screw Lock Mechanism, filed Apr. 3, 2022), the entire contents of which are incorporated by reference herein.

Figure 5:
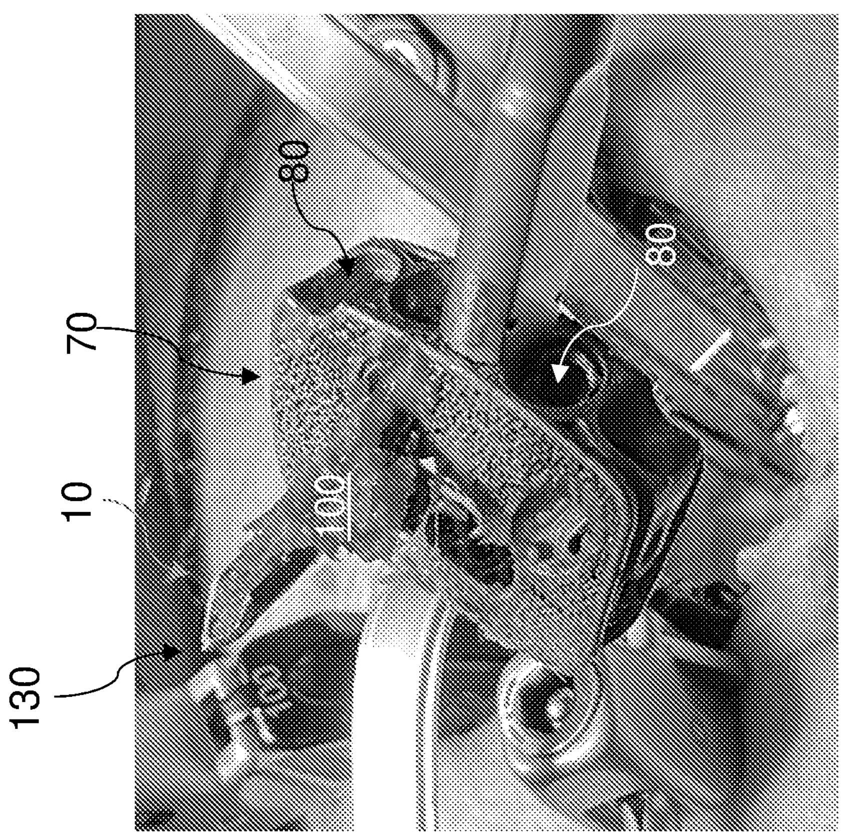
FIG. 5 illustrates a fixation nail and an interbody after removal from a patient.

Returning to FIG. 1, the body 30 of the nail 10 includes an elongated recess 90 spanning a length (L) of the body 30. In some embodiments, the elongated recess spans a majority of L. In some examples, the elongated recess 90 spans over 50 percent of L; in additional cases, over 60 percent of L; in still further cases, over 70 percent of L; and in additional cases, over 80 percent of L. In various implementations, the elongated recess 90 extends along the arcuate primary axis ($a_{pn}$) of the body 30. The elongated recess 90 may be sized to at least partially encompass tissue and/or bone during insertion into a patient. For example, the elongated recess 90 may be sized to penetrate tissue and/or bone such as to envelope, capture, and/or contain that tissue and/or bone. In certain examples, such as illustrated in the image of a removed nail 10 and interbody 70 from a patient in FIG. 5, the elongated recess 90 can envelope, capture and/or contain bone and/or tissue (tissue shown) 100. In particular cases, the nail 10 can capture or otherwise envelope tissue 100 without displacing that tissue, e.g., engaging the tissue 100 and/or bone without plastic displacement thereof. The elongated recess 90 can be sized to prevent or otherwise mitigate plastic displacement of tissue and/or bone, e.g., capturing a pocket of that tissue and/or bone as it is inserted into the vertebral body.

In certain cases, the body 30 has a reduced thickness along the elongated recess 90. For example, the elongated recess 90 can span between separate wall sections 110, 120 of the body 30 (FIG. 1). In these cases, the wall sections 110, 120 can have a thickness that is less than a base section 132 of the body 30, e.g., as measured in a direction perpendicular to the arcuate primary axis ($a_p$). In other terms, the elongated recess 90 has a width ($w_{er}$) as measured across the arcuate primary axis ($a_{pn}$), and a ratio of the combined width of the separate wall sections 110, 120 to the width ($w_{er}$) of the elongated recess 90 is approximately 0.5:1 to approximately 2:1.

In certain examples, the body 30 has a tri-point head 130 near distal end 50 for promoting insertion of the fixation nail 10 into the patient (e.g., into bone and/or tissue 100). In certain cases, at least one point 140 in the tri-point head 130 is distal relative to another point 150 in the tri-point head 130. In one example, the tri-point head 130 incudes one distal point 140 and two relatively proximal points 150A, 150B, e.g., where the two points 150A, 150B are approximately aligned in the distal-proximal direction (along axis ($a_{pn}$)). In various implementations, the tri-point head 130 provides a cutting surface during insertion of the nail 10 into the patient.

Figures 6, 7:
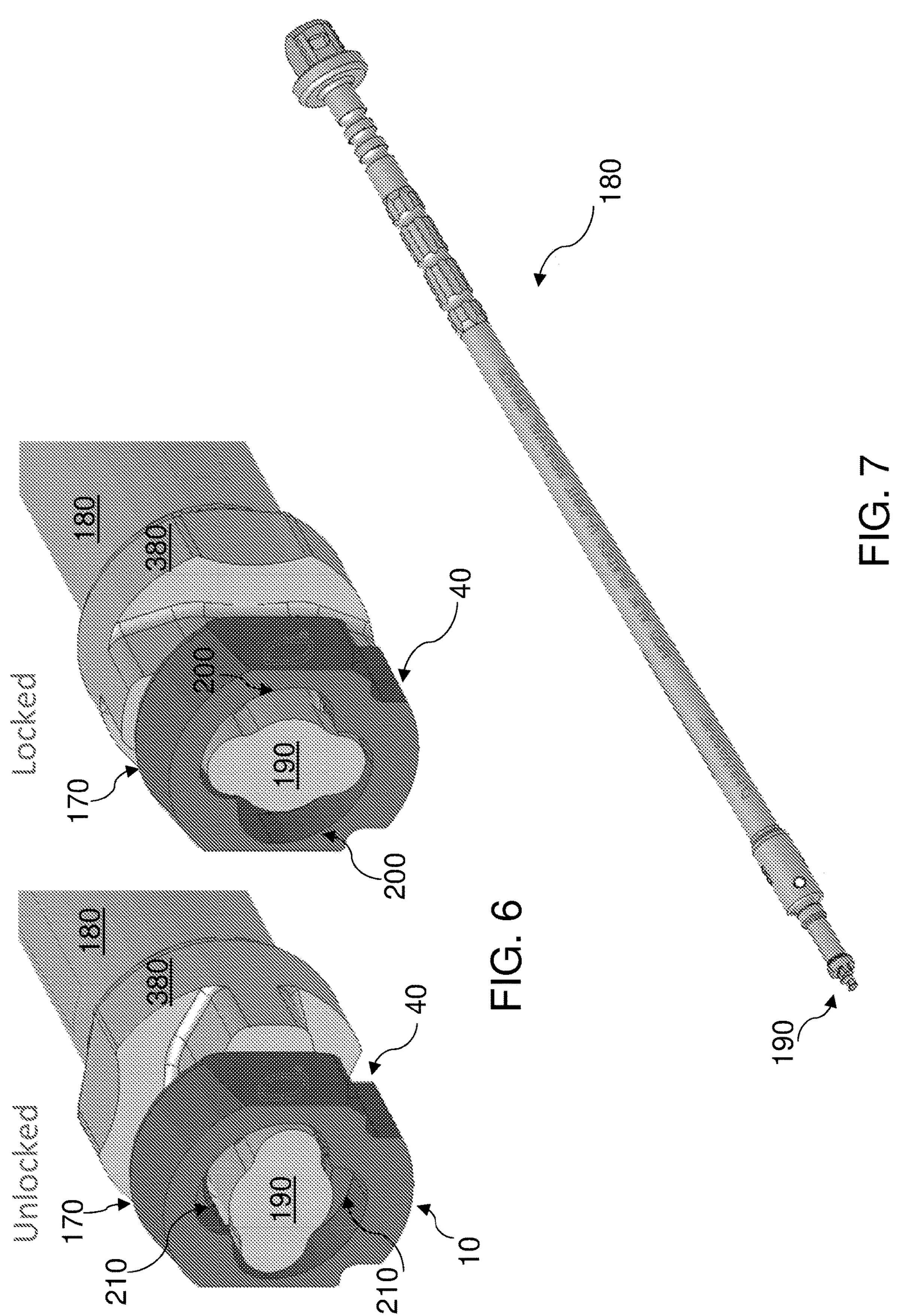
FIG. 6 illustrates a removal tool and an end section of a nail in two positions according to various implementations.
FIG. 7 is a perspective view of a removal tool according to various implementations.
Figure 8:
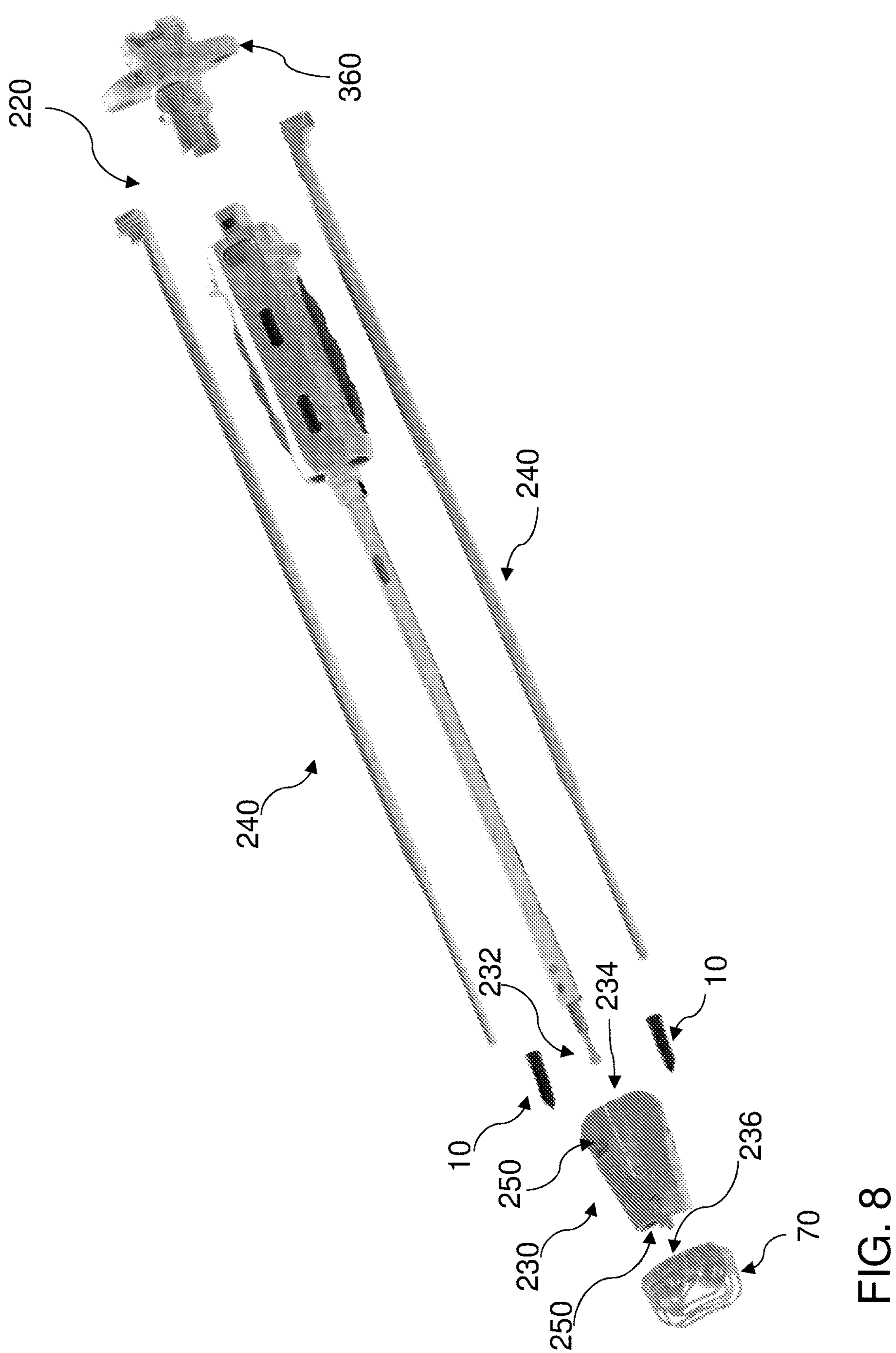
FIG. 8 shows a fusion system according to various implementations.

As described herein, in certain cases, the body 30 can also include a fin 160 extending at least partially axially along the arcuate primary axis ($a_p$) to stabilize the nail 10 in the interbody 70. In at least one embodiment, the fin 160 extends in a distal direction from the base 132 and is formed on an opposing side of the body 30 from the recess 90. Additionally, as illustrated in FIGS. 1, 6 and 7, the proximal end 40 of the body 30 can include a slot 170 sized to receive a removal tool 180 configured to remove the nail 10 from a nail guide 230 (FIG. 8). The slot 170 can be sized to receive the removal tool 180, e.g., an end 190 of the removal tool 180. FIG. 6 shows a section of the proximal end 40 of the body 30 that illustrates the interaction with the end 190 of the removal tool 180 and the slot 170. In certain cases, the slot 170 has a keyed shape that enables selective loading or unloading of the nail 10 from a nail guide 230. For example, the keyed shape can include a first slot 200 sized to receive the end 190 of the removal tool 180 and enable insertion and removal of the end 190, and a second slot 210 adjacent the first slot 200 and sized to engage the end 190 so as to couple the end 190 with the nail 10, e.g., for removal from the nail guide 230. In these cases, the first slot 200 permits movement of the end 190 relative to the nail in a first orientation (unlocked), and the second slot 210 restricts movement of the end 190 relative to the nail 10 in a second orientation (locked). In some examples, the first and second orientations are approximately perpendicular with one another, or in other terms, approximately 90 degrees offset relative to one another.

Figure 9:
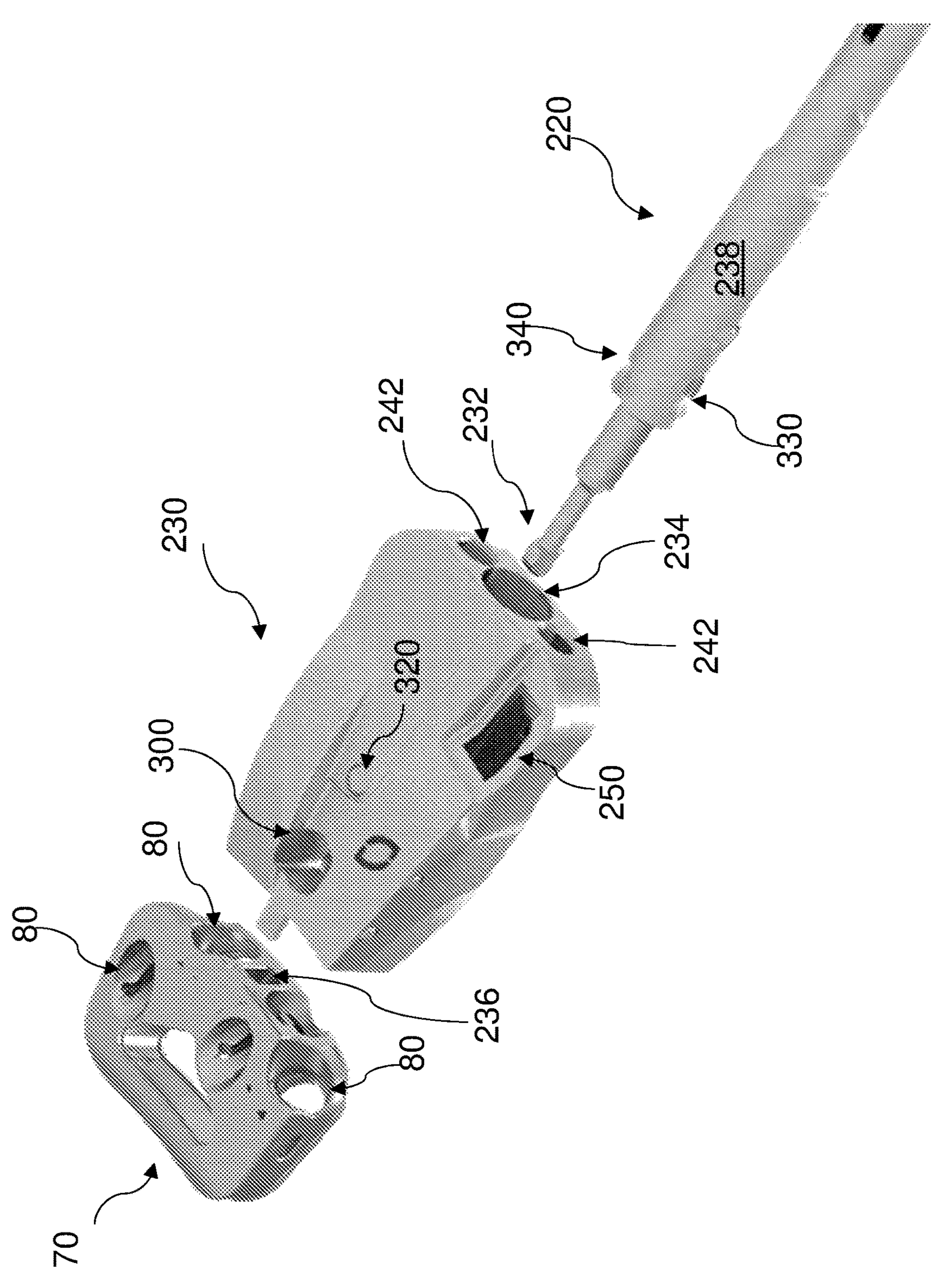
FIG. 9 is a perspective view of a portion of the fusion system in FIG. 8.
Figure 10:
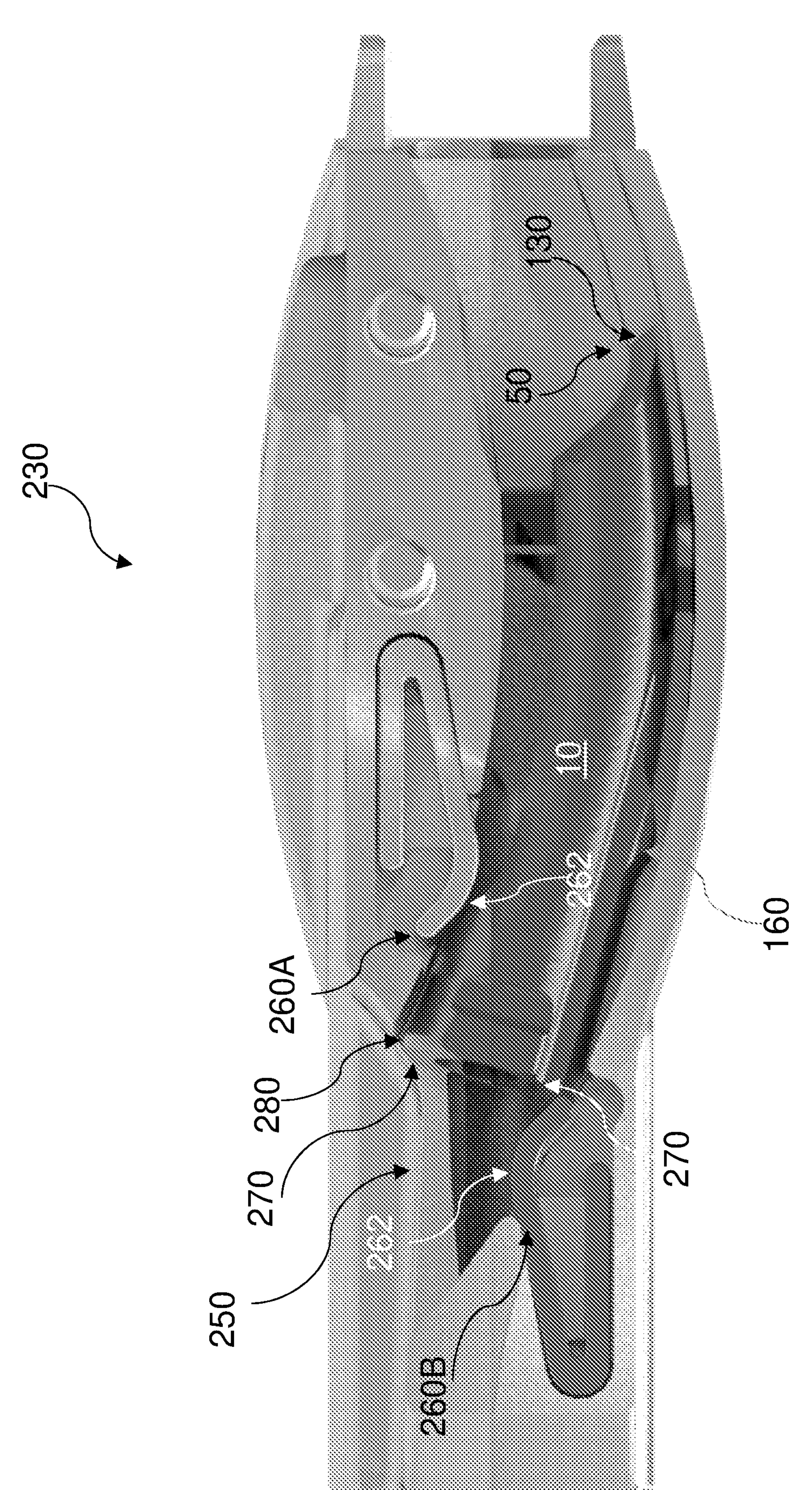
FIGS. 10-12 illustrate partial cross-sectional views of a nail guide and a nail according to various implementations.
Figure 14:
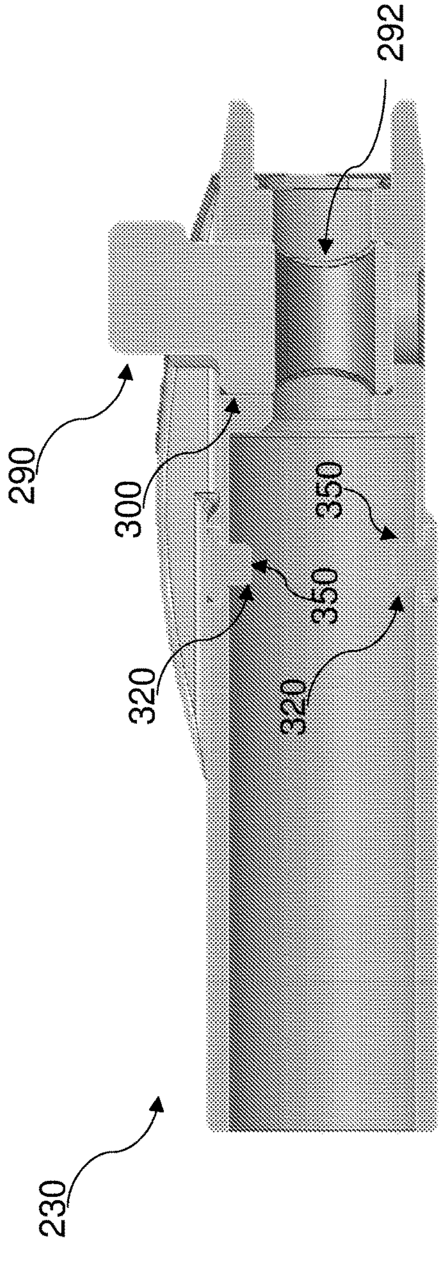
FIGS. 14 and 15 are cross-sectional views of a nail guide depicting the depth stop of FIG. 13.

FIG. 8 illustrates a system including an inserter 220 along with a nail guide 230 for deploying one or more nails 10 into an interbody 70. In various implementations, the inserter 220 includes a probe 232 (or, inner shaft) for passing through a corresponding slot 234 on the nail guide 230 and engaging a corresponding slot 236 the interbody 70. As shown e.g., in FIGS. 14 and 15, when passing the inserter 220 through slot 234, a shaft (e.g., outer shaft) 238 of the inserter 220 is configured to engage the nail guide 230. As such, when engaged, the interbody 70, nail guide 230, and inserter 220 are fixed relative to one another. FIG. 8 also illustrates a set of (e.g., two) impactors 240 for engaging slots 242 in the nail guide, and deploying the (pre-loaded) nail(s) 10 from the nail guide 230 to the interbody 70. FIG. 9 shows a close-up view of the nail guide 230 and the body of the inserter 220. As noted herein, the nail(s) 10 is configured to be pre-loaded into nail slot(s) 250 in the nail guide 230 before insertion into a patient. In particular examples, the nail guide 230 includes two nail slots 250, one on each of a top and bottom of the nail guide body. In certain cases, during a fusion procedure, the interbody 70 is positioned in the vertebral space prior to deploying nail(s) 10 to retain that interbody 70 in place in the spinal column (FIGS. 3, 4). In certain cases, the nail(s) 10 are loaded into a nail slot(s) 250 in the nail guide 230 and then the nail guide 230 is inserted into the incision in the patient to facilitate delivery of nail(s) 10 to the interbody 70. As described herein, in particular cases, nail(s) 10 are loaded into the nail guide 230 (e.g., by hand) prior to positioning the interbody 70 in vertebral space. FIG. 10 shows a cross-section of the nail guide 230 illustrating details of positioning of one nail 10 in a first position in a nail slot 250. In various implementations, as shown in FIG. 9, the nail guide 230 is configured to accommodate multiple nails 10, e.g., two or more nails 10 in corresponding nail slots 250 for deploying to the interbody 70.

Figures 11, 12:
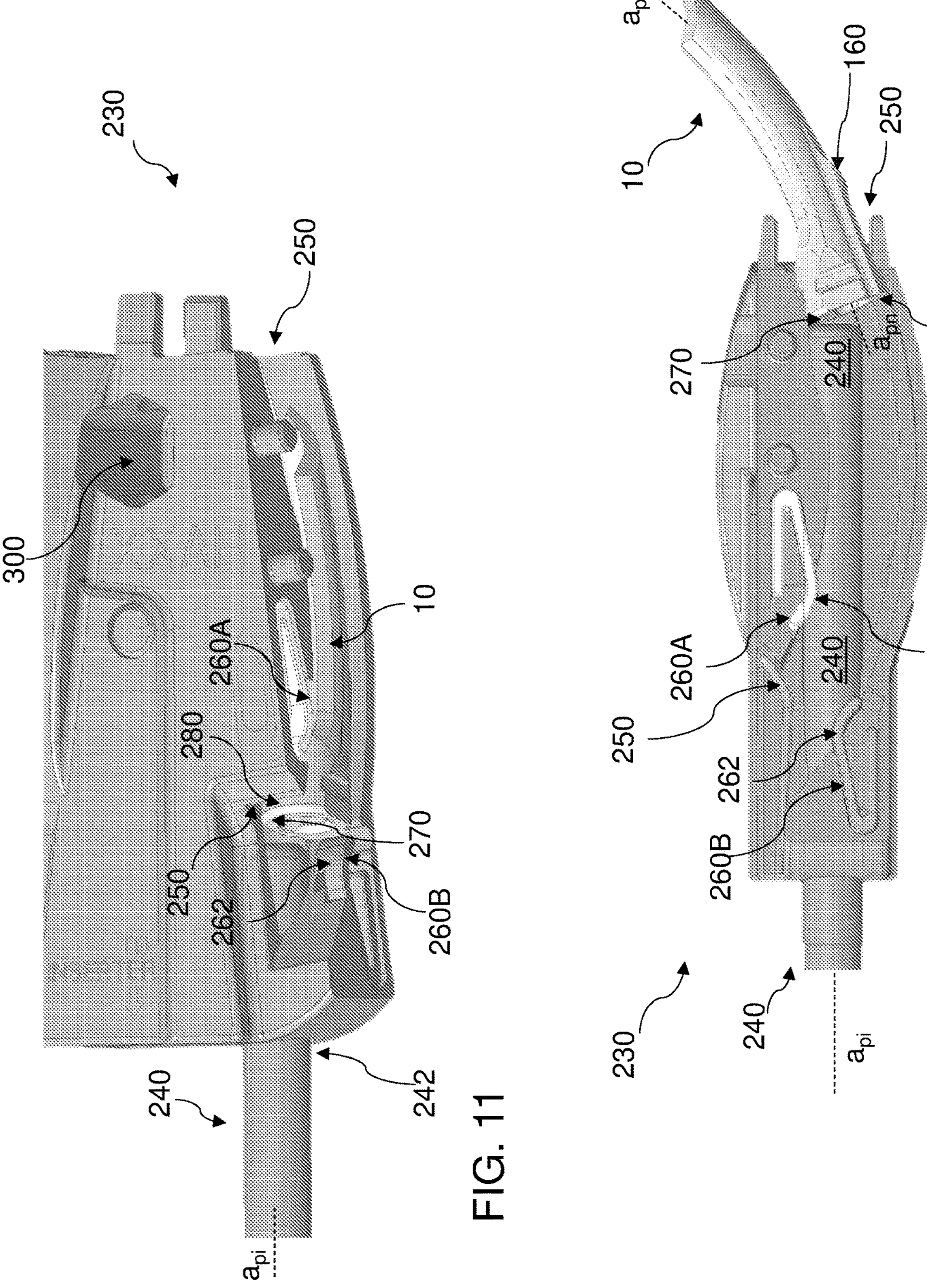
Figure 13:
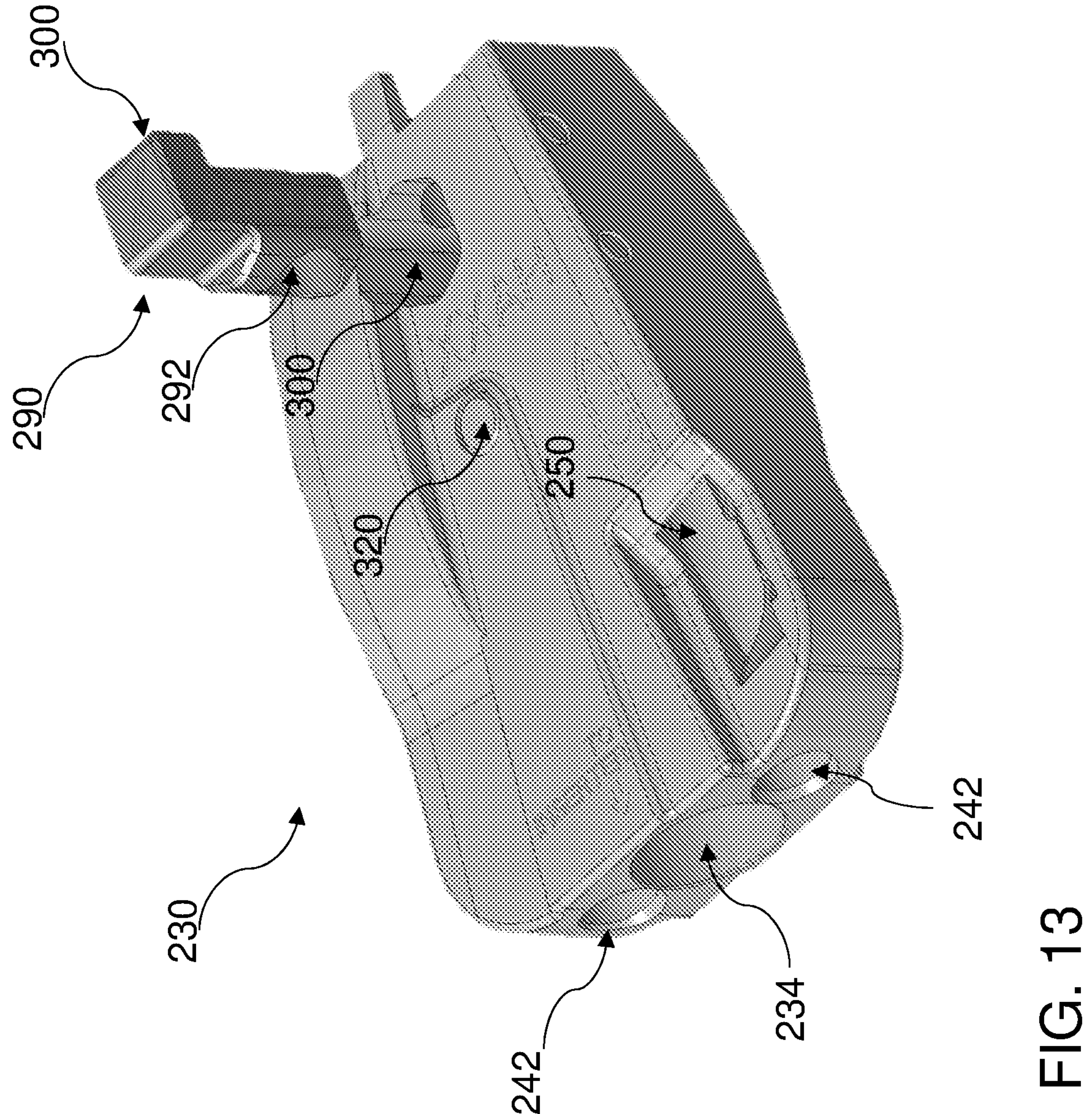
FIG. 13 is a perspective view of a nail guide illustrating a depth stop according to various implementations.

Returning to FIG. 10, and with reference to the perspective view of a nail 10 in the first position in nail guide 230 in FIG. 11, at least one biasing mechanism 260 controls deploying the nail(s) 10 to through-hole(s) 80 in the interbody 70. In some cases, the biasing mechanism(s) 260 provide audible and/or tactile feedback that a nail 10 is secured in the nail guide 230, e.g., a force-and-release mechanism and/or an audible clicking sound to indicate that the nail 10 is secured by the biasing mechanism(s) 260. In certain examples, a first biasing mechanism 260A controls deploying the nail 10 to the through-hole 80 (FIG. 9). In additional examples, a second biasing mechanism 260B prevents unintentional discharge of the nail 10 from the nail guide 230, e.g., unintentional discharge causing the nail 10 to back out of the nail slot 250. In some examples, at least one of the biasing mechanism(s) 260 includes a spring or a retractable protrusion for engaging a surface of the nail 10. In other examples, the biasing mechanism(s) 260 include any deformable component that has a spring-like quality to return to form, e.g., permitting a nail 10 to pass when sufficient normal force is applied to the biasing mechanism 260. In certain cases, such as illustrated in FIGS. 10-12, each biasing mechanism 260 includes an arcuate contact surface 262 configured to contact a portion of the nail 10 to limit movement within the nail slot 250 when engaged, but permit the nail 10 to pass the biasing mechanism 260 when sufficient force is applied (e.g., via an impactor). In a particular example, as illustrated in FIG. 9, the nail 10 can be loaded into a nail slot 250, e.g., by hand, where biasing mechanism 260B prevents unintentional back-out (discharge from the rear (proximal) end of slot 250), and biasing mechanism 260A prevents unintentional discharge from the forward (distal) end of the slot 250. The two biasing mechanisms 260A,B can work in concert to secure the nail 10 in slot 250, and prevent rattling and/or discharge. In various implementations, as illustrated in FIGS. 11 and 12, biasing mechanism 260B retains the nail 10 at a sufficient depth in the slot 250 such that the impactor 240 can engage the nail 10 to deploy the nail 10 through the distal end of slot 10. In particular cases, during deployment, the force of the impactor 240 on nail 10 will be sufficient to overcome the biasing mechanism 260A and enable the nail 10 to be deployed from the distal end of slot 250 into the slots 80 in the interbody 70.

FIG. 12 shows a cross-section of nail guide 230 with the nail 10 in a second position, i.e., during deployment from the nail guide 230 and into the interbody 70 (not shown). In certain cases, during deployment, the impactor 240 drives the nail 10 through the nail slot 250 to the through-hole(s) 80 in the interbody 70. In some examples, e.g., as illustrated in FIGS. 11 and 12, the impactor 240 has a primary axis ($a_{pi}$) that is off-axis relative to the primary axis ($a_{pn}$) of the nail 10. That is, the primary axis ($a_{pi}$) of impactor 240 is an approximately linear, or straight line, while the primary axis ($a_{pn}$) of the nail 10 is arcuate, e.g., to complement the arcuate shape of the nail slot 250. In additional terms, the primary axis ($a_{pi}$) of impactor 240 is also offset relative to the proximal end 40 of the body 30, such that the impactor 240 contacts an approximately flat section 270 of the body 30 proximate to the slot 170 off-center relative to the slot 170 (e.g., axially off-center). In certain cases, the approximately flat section 270 of the body 30 is configured to aid in retaining the nail 10 in the nail slot 250 by engaging at least one of the biasing mechanisms 260, e.g., the second biasing mechanism 260B. In particular cases, the approximately flat section 270 of the body 30 engages the second biasing mechanism 260B after initial loading into the nail guide 230, and a surface 280 on the approximately flat section 270 is positioned to engage the first biasing mechanism 260A during deployment of the nail 250 from the distal end of slot 250.

Figure 15:
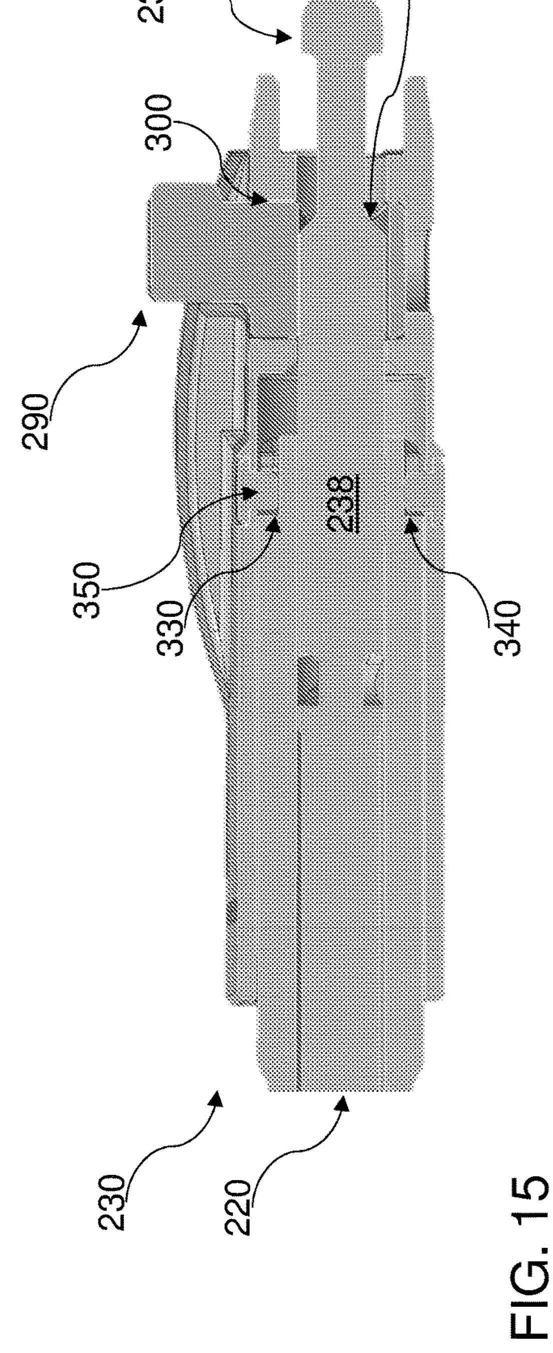
Figure 16:
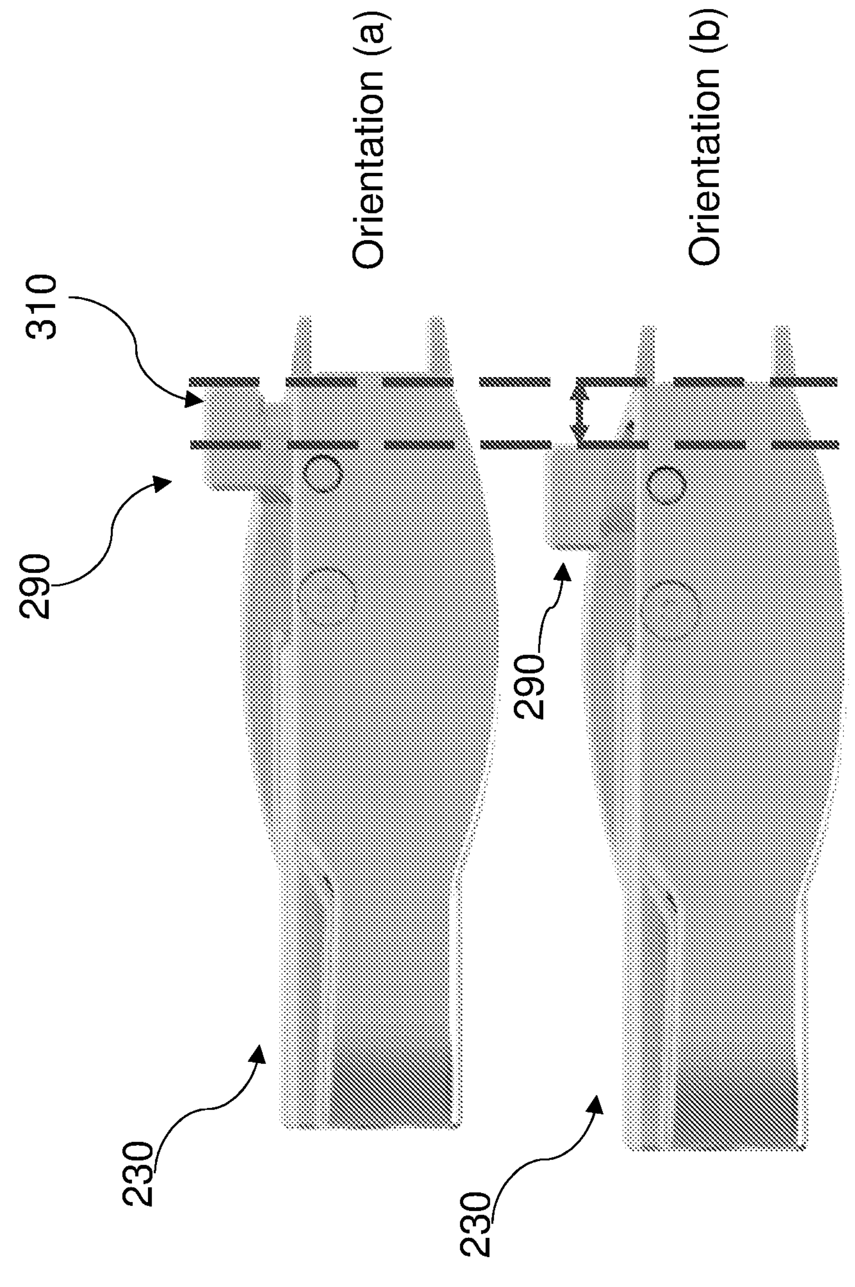
FIG. 16 is a side view of a nail guide illustrating the depth stop in distinct orientations.

In certain implementations, for example as illustrated in FIGS. 13-16, the nail guide 230 may further include a depth stop 290 configured to control a position of the interbody 70 during deployment of the nail 10 into the interbody 70. In certain cases, as shown in FIG. 15, the depth stop 290 is positioned to prevent over-deployment of the interbody 70, e.g., where the distal surface of the depth stop 290 contacts the vertebral body to limit movement of the interbody 70. The depth stop 290 can include an internal slot 292 that is sized to allow the inserter to 220 to pass without interference. In particular cases, for example as shown in FIG. 16, the depth stop 290 is removable and/or reversable for flush and/or countersink configurations. In these cases, the depth stop 290 is sized to fit in a depth stop slot 300 in the nail guide 230 in at least two orientations. In a first orientation (a), the depth stop 290 limits insertion of the interbody 70 to a first depth (measured along the proximal-distal depth of the nail guide), and in a second orientation (b), the depth stop 290 limits insertion of the interbody 70 to a second, distinct depth. In further examples, the system can be configured to accommodate distinct nail guides 230 of distinct sizes, each with correspondingly sized depth stops 290. According to some implementations, each of the distinctly sized depth stops 290 (i.e., inserts) includes a mating feature that prevents loading into a nail guide 230 that does not correspond with that sized depth stop 290. For example, each depth stop 290 can include a "mistake-proofing" or "poka-yoke" feature such as an orientation-dependent mating feature that can only allow loading of the depth stop 290 in only one sized slot 300. In certain examples, the depth stop 290 can include an asymmetric protrusion 310 that is configured to limit the depth at which the interbody 70 can be loaded into the vertebral body.

Figure 17:
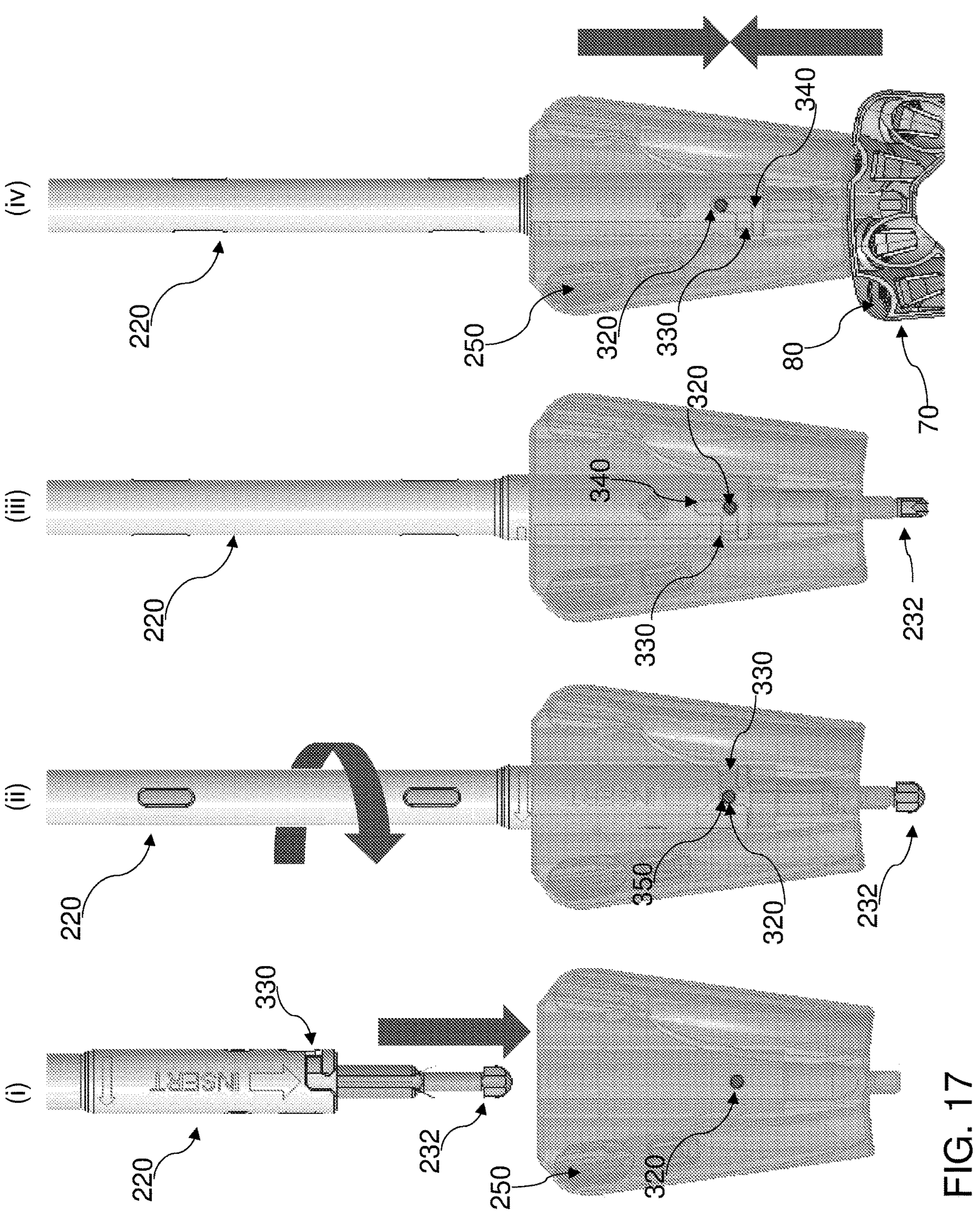
FIG. 17 illustrates a process of coupling an inserter to a nail guide according to various implementations.

According to various implementations, e.g., as shown in the partially transparent view of nail guide 230 in FIG. 17, the nail guide 230 also includes a locking mechanism 320 configured to engage a complementary locking mechanism 330 on the inserter 220. In particular, FIG. 17 illustrates a process of inserting and engaging an inserter 220 into nail guide 230 in processes (i)-(iv). In various implementations, the locking mechanism 330 on the inserter 220 includes a multi-segment slot 340 and the complementary locking mechanism 320 on the nail guide 230 includes a tab 350 complementing a portion of the multi-segment slot 340 (e.g., two slots 340 and two tabs 350 shown in FIGS. 9, 14, and 15). In various implementations, the multi-segment slot 340 includes at least two sections that have distinct orientations, e.g., two sections with approximately perpendicular orientations.

Figure 18:
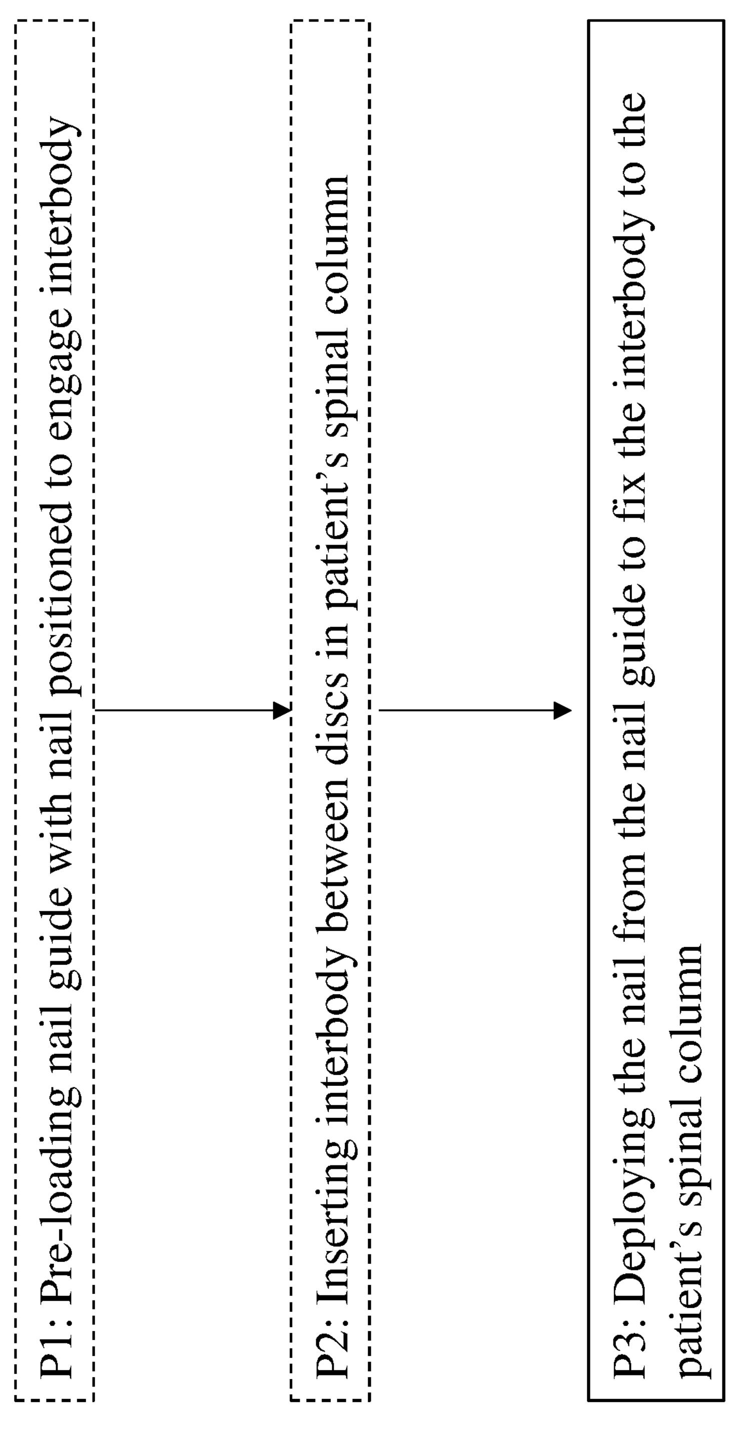
FIG. 18 is a flow diagram illustrating processes in a method according to various implementations.

FIG. 18 is a flow diagram illustrating processes in a method of placing an interbody 70 in a patient's spinal column according to various implementations. In certain cases, the method is part of an anterior lateral interbody fusion (ALIF) procedure or a lateral ALIF procedure. These procedures are not limiting of the disclosed methods and apparatuses, which may be applicable to other surgical procedures. With reference to FIG. 18, as well as the apparatus in FIGS. 8-12, a first process (P1) in the method can include pre-loading the nail guide 230 with the nail 10 positioned to engage the interbody 70 and the patient's spinal column. As described herein, a plurality of nails 10 (e.g., two or more) can be pre-loaded into the nail guide 230 in a single process, e.g., by hand. A second process (P2) can include inserting the interbody 70 between discs in a patient's spinal column. Aspects of inserting an interbody 70 into a patient's spinal column, and related procedures, are described in PCT Application No. US 2022/023224 (Spinal Implant with Flexible Screw Lock Mechanism, filed Apr. 3, 2022), the entire contents of which are incorporated by reference herein. In various implementations, processes P1 and P2 can be performed simultaneously, or in a different order (e.g., P2 prior to P1). As noted herein, the nail guide 230 can be loaded with nail(s) 10 prior to inserting the nail guide 230 into the incision proximate to the patient's spinal column.

In various implementations, e.g., as shown in FIGS. 8-12 pre-loading the nail guide 230 with nail(s) 10 includes inserting the nail 10 in the nail slot 250 in the nail guide 230. As the nail 10 is inserted in the nail slot 250, the nail 10 engages with the first biasing mechanism 260A, and subsequently engages with the second mechanisms 260B to retain the nail 10 in the nail slot 250. As noted herein, a user can insert the nail 10 through each nail slot 250 in the nail guide 230, e.g., by hand. Prior to inserting nail(s) 10 in nail slot(s) 250, simultaneously with that insertion, or afterward, the inserter 220 can be secured to the nail guide 230, such that the primary axis ($a_{pi}$) of the impactor 240 is off-axis with the primary axis ($a_{pn}$) of the nail 10 during insertion. In one example, the inserter 220 is coupled with the nail guide 240 prior to inserting nails 10 in nail slots 250. In certain cases, the inserter 220 can engage the slot 234 in the nail guide 230 to secure the inserter 220 to the nail guide 230 (FIG. 17). In various implementations, a handle 360 on the inserter 220 can be actuated to engage the probe (or, inner shaft 232) with the slot 236 in the interbody 70.

After the inserter 220 is secured to the nail guide 230, in a third process (P3), the impactor(s) 240 are used to deploy the nail(s) 10 from the nail guide 230 to fix the interbody 70 to the patient's spinal column (FIG. 12). In such cases, the impactor(s) 240 are actuated (e.g., manually via a driver tool such as a mallet) to drive the nail 10 from the nail slot 250 in the nail guide 230 into the through-hole 80 in the interbody 70 and to engage the patient. As described herein, the elongated recess 90 enables the nail 10 to engage the tissue and/or bone of the patient without substantially displacing that tissue, e.g., engaging the tissue and/or bone without plastic displacement thereof. In various implementations the fin 160 and the flat section 270 on the nail 10 can engage a retention feature 370 on the through-hole 80 in the interbody 70 to retain the nail 10 in the interbody 70 while engaging the patient's tissue and/or bone proximate the interbody 70, e.g., as shown in FIGS. 3 and 4. In a particular example as shown in FIGS. 3 and 4, the through-hole 80 to the interbody 70 can include retention feature 370, e.g., a lip, deflectable latch, retractable tab or spring element that is configured to engage a portion of the fin 160 and/or the approximately flat section 270 of the nail 10 once deployed into the opening 80. Additional description of example retention features 370 (e.g., a lip) are described relative to the interbody disclosed in in PCT Application No. US 2022/023224, previously incorporated by reference herein. In various implementations, the interbody 70 is configured to engage the nail 10 and retain the nail 10 in contact with the patient's tissue and/or bone without a threaded connection.

In various implementations, referring back to FIGS. 6 and 7, the removal tool 180 can be used to engage the proximal end 40 of the nail 10 for removal of the nail 10 from the nail guide 230 via a non-threaded mechanism. For example, after a nail 10 has been inserted into the nail guide 230, removal of that nail 10 may be desirable (e.g., to replace with a nail of a different size). The keyed slot 200 at the proximal end 40 of the nail 10 can be engaged with the end 190 on the removal tool 180 by first inserting the end 190 in one orientation and then rotating or otherwise reorienting the end 190 to a distinct orientation to engage the nail 10 in the keyed slot 200. Once engaged, the removal tool 180 can be used to pull the nail 10 from the interbody 70. In various implementations, such as where the interbody includes a retention feature 370 such as a latch lock, the removal tool 180 includes a ridge 380 for engaging the latch lock to enable removal of the nail 10 from the nail guide 230. In such cases, when the removal tool 180 is placed into the second orientation (FIG. 6), the ridge 380 engages the latch lock (e.g., retention feature 370) and enables the nail 10 to be pulled back out of the interbody 70 by the removal tool 180.

As noted herein, the fixation nails (or, blades), systems, and related approaches disclosed according to various implementations provide numerous benefits relative to conventional fixation devices and systems. For example, the disclosed fixation nails, fixation systems, and methods can enhance efficacy of spinal procedures, as well as mitigate operator (e.g., surgeon) error in performing such procedures. The disclosed fixation nails, systems, and approaches can be beneficial for both supine anterior lateral interbody fusion (ALIF) procedures and lateral ALIF procedures. The various disclosed implementations can mitigate or obviate use of complicated and/or unwieldy surgical instruments such as U-joint mounts or instruments for actuating bone awls, screw drivers that require multi-step access to the vertebral body. For example, a fixation nail that does not include a threaded coupling such as those disclosed herein can mitigate or obviate the use of screw drivers in coupling an interbody to a patient's bone and/or tissue. Further, a fixation nail with a recess such as those disclosed herein can mitigate resistance from bone and/or tissue when loading the nail through an interbody. Even further, a nail guide that enables pre-loading of nails such as those disclosed herein can allow the surgeon or other surgical professional to reduce surgical time and processes performed in or around the surgical access point. Relative to conventional approaches, the fixation nail, nail guide, systems and methods can also enable less invasive (e.g., smaller) incisions to the patient for access to the vertebral body.

In various implementations, components described as being "coupled" to one another can be joined along one or more interfaces. In some implementations, these interfaces can include junctions between distinct components, and in other cases, these interfaces can include a solidly and/or integrally formed interconnection. That is, in some cases, components that are "coupled" to one another can be simultaneously formed to define a single continuous member. However, in other implementations, these coupled components can be formed as separate members and be subsequently joined through known processes (e.g., soldering, fastening, ultrasonic welding, bonding). In various implementations, electronic components described as being "coupled" can be linked via conventional hard-wired and/or wireless means such that these electronic components can communicate data with one another. Additionally, sub-components within a given component can be considered to be linked via conventional pathways, which may not necessarily be illustrated.

Unless otherwise defined, all technical terms used herein have the same meaning as commonly understood by one of ordinary skill in the art to which this invention belongs. As used in this specification and the appended claims, the singular forms "a," "an," and "the" include plural references unless the context clearly dictates otherwise. Any reference to "or" herein is intended to encompass "and/or" unless otherwise stated. As used in this specification and the claims, unless otherwise stated, the term "about," "approximately," "generally," and "substantially" refers to variations of less than or equal to +/−1%, +/−2%, +/−3%, +/−4%, +/−5%, +/−6%, +/−7%, +/−8%, +/−9%, +/−10%, +/−11%, +/−12%, +/−14%, +/−15%, +/−16%, +/−17%, +/−18%, +/−19%, or +/−20%, depending on the embodiment. As a further non-limiting example, about 100 millimeters represents a range of 95 millimeters to 105 millimeters, 90 millimeters to 110 millimeters, or 85 millimeters to 115 millimeters, depending on the embodiments.

While inventive features described herein have been described in terms of preferred embodiments for achieving the objectives, it will be appreciated by those skilled in the art that variations may be accomplished in view of these teachings without deviating from the spirit or scope of the invention. Also, while this invention has been described according to a preferred use in spinal applications, it will be appreciated that it may be applied to various other uses desiring surgical fixation, for example, the fixation of long bones.

A number of implementations have been described. Nevertheless, it will be understood that additional modifications may be made without departing from the scope of the inventive concepts described herein, and, accordingly, other implementations are within the scope of the following claims.

We claim:

1. A fixation nail for an interbody fusion procedure, the fixation nail comprising:

a body having an arcuate primary axis extending from a distal end to a proximal end thereof, wherein the body has an outer surface that enables complete insertion and removal of the fixation nail into an interbody without threaded engagement, and wherein the body includes an elongated recess spanning a majority of a length of the body, the elongated recess sized to at least partially encompass at least one of tissue or bone during insertion into a patient, wherein the fixation nail is positioned within an inserter and a nail guide for deployment, the inserter includes a probe for passing through a corresponding slot on the nail guide, when passing the inserter through the slot, a shaft of the inserter is configured to engage the nail guide, the fixation nail and the inserter are fixed relative to one another when engaged, wherein the nail guide includes two nail slots, and a first and second biasing mechanism, the first and second biasing mechanism including an arcuate contact surface configured to contact a portion of the nail to limit movement within the nail slot when engaged and permits the nail to pass the biasing mechanism when force is applied.

2. The fixation nail of claim 1, wherein the outer surface is thread-free.

3. The fixation nail of claim 1, wherein the elongated recess extends along the arcuate primary axis of the body.

4. The fixation nail of claim 1, wherein the body has a reduced thickness along the elongated recess.

5. The fixation nail of claim 1, wherein the elongated recess spans between separate wall sections of the body.

6. The fixation nail of claim 5, wherein the separate wall sections have a combined width as measured across the arcuate primary axis, the elongated recess has a width as measured across the arcuate primary axis, and a ratio of the combined width of the separate wall sections to the width of the elongated recess is approximately 0.5:1 to approximately 2:1.

7. The fixation nail of claim 1, wherein the body includes a tri-point head near the distal end for promoting insertion of the fixation nail into the patient.

8. The fixation nail of claim 7, wherein at least one point in the tri-point head is distal relative to another other point in the tri-point head.

9. The fixation nail of claim 7, wherein two points in the tri-point head are approximately aligned in a distal-proximal direction.

10. The fixation nail of claim 7, wherein the tri-point head provides a cutting surface during insertion of the fixation nail into the patient.

11. The fixation nail of claim 1, wherein the fixation nail is configured to be pre-loaded into a nail guide before insertion into the patient.

12. The fixation nail of claim 1, wherein the body includes a fin extending at least partially axially along the arcuate primary axis to stabilize the fixation nail in the interbody.

13. The fixation nail of claim 1, wherein the proximal end of the body includes a slot sized to receive a removal tool for removing the fixation nail from the interbody.

14. The fixation nail of claim 13, wherein the body includes at least one approximately flat section proximate the slot for engaging a biasing mechanism on the interbody.

15. The fixation nail of claim 13, wherein the slot has a keyed shape.

16. The fixation nail of claim 15, wherein the keyed shape enables selective loading or unloading of the fixation nail from the interbody.

17. The fixation nail of claim 1, wherein the body is additively manufactured.

18. The fixation nail of claim 1, wherein the fixation nail is one of a plurality of fixation nails of distinct size, and wherein the body includes at least one indicator of a size of the fixation nail.

19. The fixation nail of claim 1, wherein the fixation nail is compatible with a supine anterior lateral interbody fusion (ALIF) procedure and a lateral ALIF procedure.

* * * * *